US00PP28139P2

(12) United States Plant Patent
Cully

(10) Patent No.: US PP28,139 P2
(45) Date of Patent: Jun. 27, 2017

(54) RED MAPLE TREE NAMED 'MILLER'

(50) Latin Name: *Acer rubrum*
Varietal Denomination: Miller

(71) Applicant: Earl Cully, Jacksonville, IL (US)

(72) Inventor: Earl Cully, Jacksonville, IL (US)

(73) Assignee: Earl Cully, Jacksonville, IL (US)

( * ) Notice: Subject to any disclaimer, the term of this patent is extended or adjusted under 35 U.S.C. 154(b) by 167 days.

(21) Appl. No.: 13/999,437

(22) Filed: Feb. 26, 2014

(51) Int. Cl.
*A01H 5/00* (2006.01)

(52) U.S. Cl.
USPC ..... Plt./224

(58) Field of Classification Search
USPC ..... Plt./216, 224
See application file for complete search history.

*Primary Examiner* — Susan McCormick Ewoldt
*Assistant Examiner* — Karen Redden

(57) ABSTRACT

A new and distinct red maple tree named 'Miller' characterized by its broad rounded growth habit, green mildew-resistant foliage, strong wood, and early autumn coloration.

6 Drawing Sheets

Latin name genus and species of the plant claimed: *Acer rubrum.*

Variety denomination: 'Miller'.

The present invention comprises a new and distinct cultivar of red maple tree, botanically known as *Acer rubrum* and referred by the cultivar name 'Miller'. The initially discovered tree is growing in a cultivated area on the home grounds of the inventor Earl Cully, 846 Hoagland Road, Jacksonville, Ill. 62650, in Morgan County, in Township 14, Range 10. Asexual clones of this tree have been propagated by softwood cuttings in June and are currently growing in the arboretum at 846 Hoagland Road, Jacksonville, Ill. 62650.

The new cultivar was selected because it possesses a 45-60° angle of branching and well rounded, crown form with bright red fall color that typically begins to develop in the third week of September before other red maple cultivars such as Red Sunset® 'Franksred', October Glory®, and Burgundy Belle® 'Magnificent Magenta' U.S. Plant Pat. No. 7,222. The red maple cultivars October Glory®, Red Sunset® 'Franksred' are also growing at the inventor's home grounds and they typically develop fall color in mid to late October. The new cultivar 'Miller' develops peak fall color two to three weeks before Red Sunset® 'Franksred' or October Glory® red maple cultivars. The 'Miller' cultivar develops scarlet red autumn foliage (FIG. 5) that holds until leaf senescence. This trait differs from 'Magnificent Magenta' autumn foliage that changes from burgundy to scarlet before leaf senescence.

The parent tree possesses a broad rounded crown form approximately 36 feet (11 meters) in average diameter with no sign of structural failure (FIG. 1). The trunk is approximately 4 feet (1.3 meters) in circumference or 15 inches (38 cm) d.b.h. (diameter at breast height) measured 4.5 feet (137 cm) above the ground. The original tree is 36 feet (11 meters) in height and is approximately 44 years of age. Visual inspection shows the original tree to be free of any defects with no sign of any breakage along the bole or in the crown, and it appears to be in excellent health with good vigor. The leaves are a medium green on the upper surface and a pale green on the under surface (FIG. 4). The foliage is free from most foliar diseases including powdery mildew.

The leaves turn a scarlet red color in autumn (FIG. 5) before senescence starting in late September in central Illinois.

The broad rounded crown form of the 'Miller' cultivar lends itself to park, shade tree plantings on home lawns, city parks, streets, and industrial sites (FIG. 2). In two to three years after asexual propagation, the tree begins to develop a similar crown form as the parent tree with very little if any pruning necessary (FIG. 3). This crown form is more compact and dense than most seedling-grown red maple. The foliage is highly resistant to powdery mildew. The original tree has never suffered from any observable structural failures and shows no sign of decay anywhere on the bole, trunk flare, or crown.

Asexually propagated trees of the 'Miller' cultivar come true to form with the same rounded crown form as the initially discovered tree and early scarlet fall color (FIG. 6). The leaves and fruit of asexually propagated trees are identical to the original tree.

BRIEF DESCRIPTION OF THE DRAWINGS

The accompanying colored photographs illustrate the appearance and color of the new 'Miller' red maple tree. These photographs show the color as accurately as is reasonably possible to obtain in colored reproductions of this type. Actual foliage colors may differ slightly due to light reflectance.

DETAILED BOTANICAL DESCRIPTION

Figure 1:
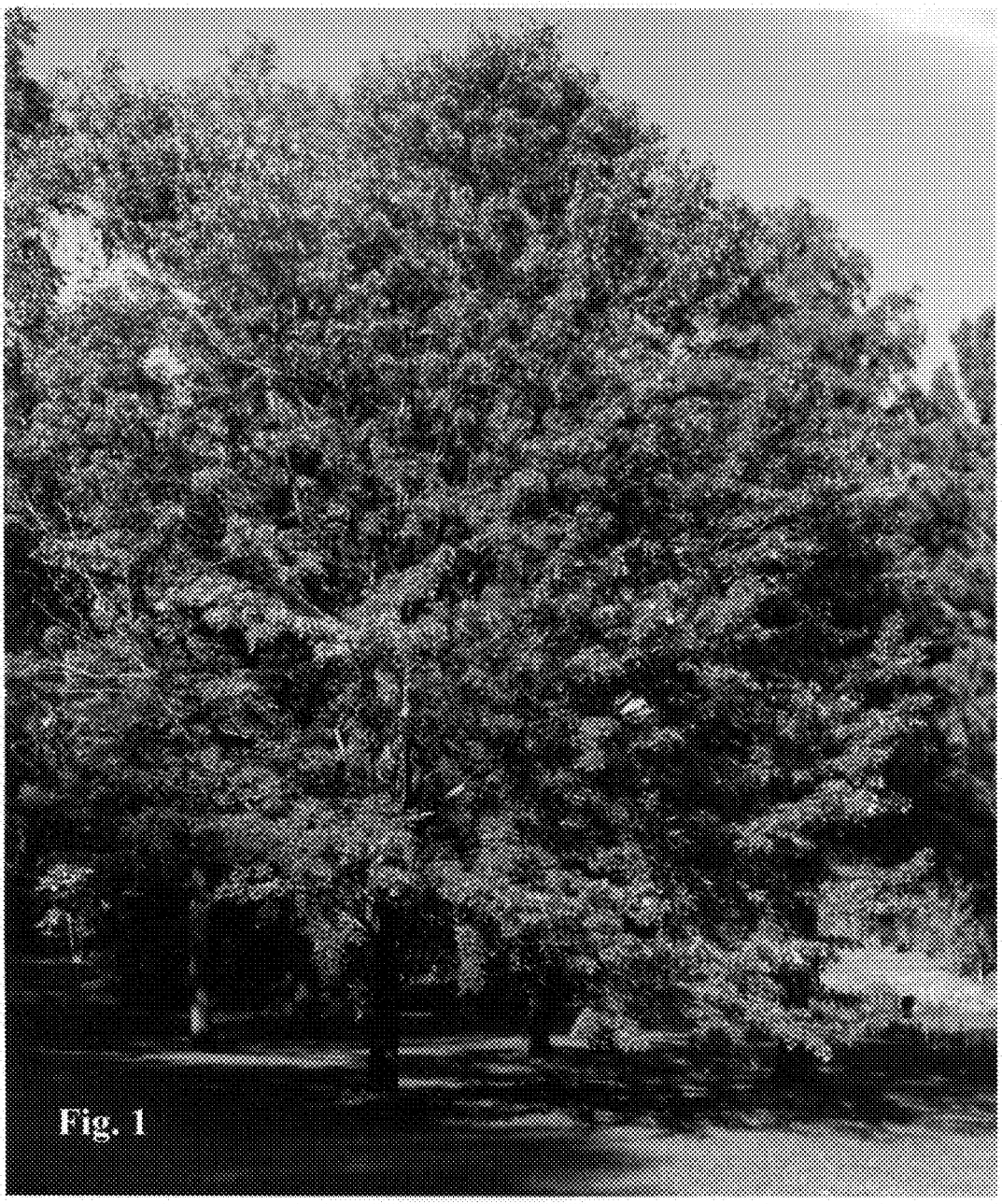
FIG. 1 depicts the initially discovered tree named 'Miller' in summer showing its rounded crown form at approximately 39 years old
Figure 2:
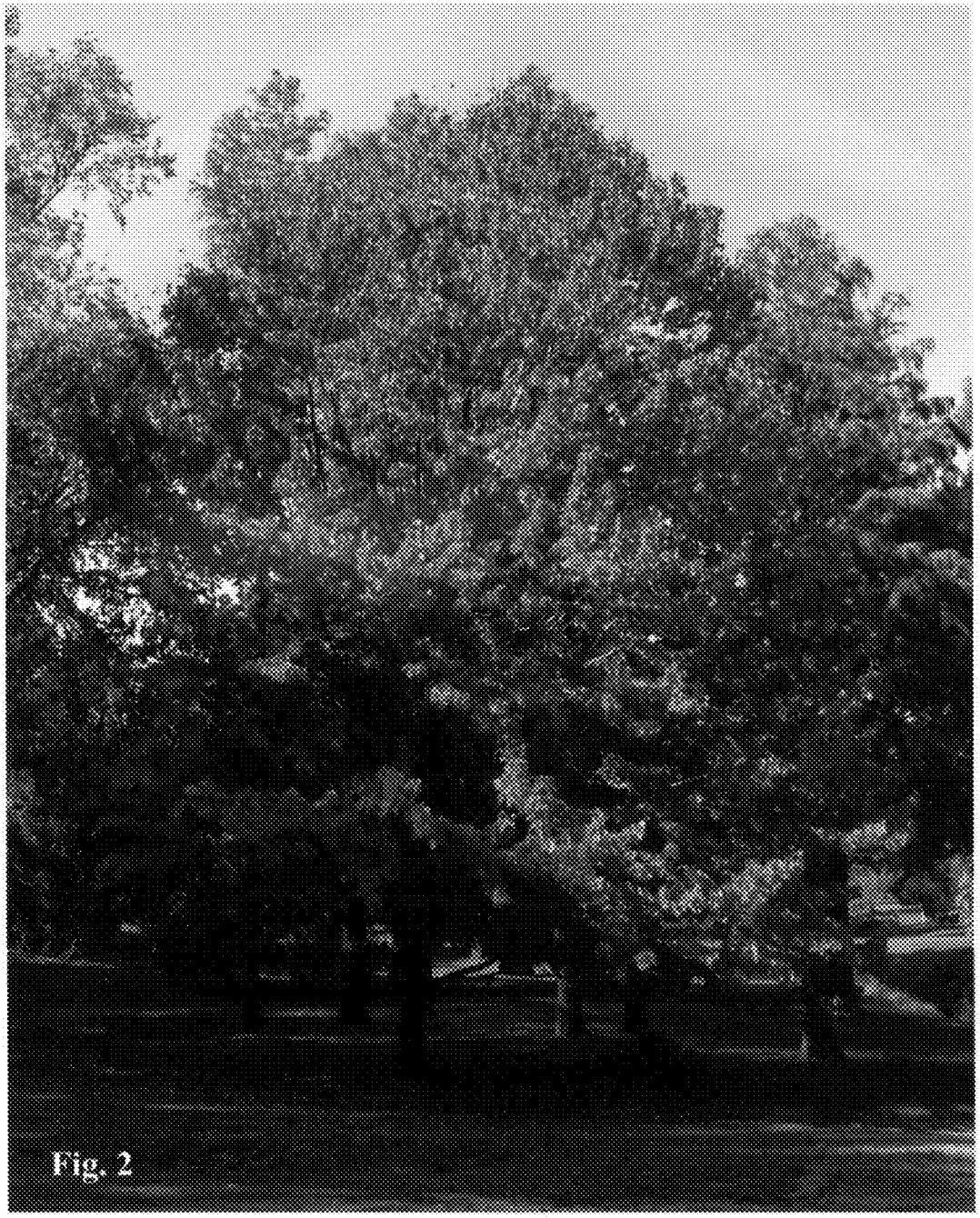
FIG. 2 depicts the 'Miller' cultivar maple tree with autumn foliage at approximately 39 years old.
Figure 3:
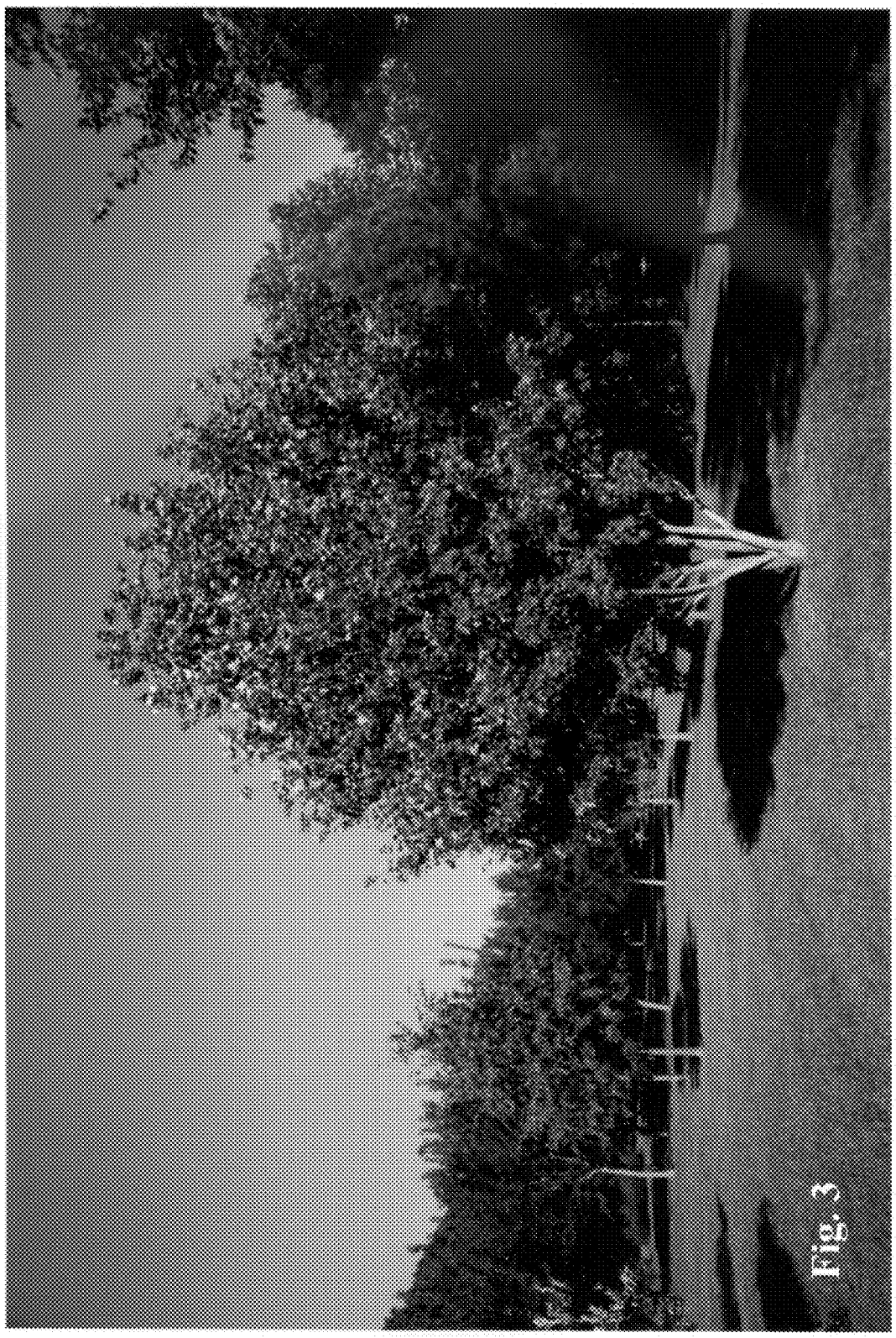
FIG. 3 depicts the first asexually propagated tree of the 'Miller' cultivar in summer foliage at 15 years old.
Figure 4:
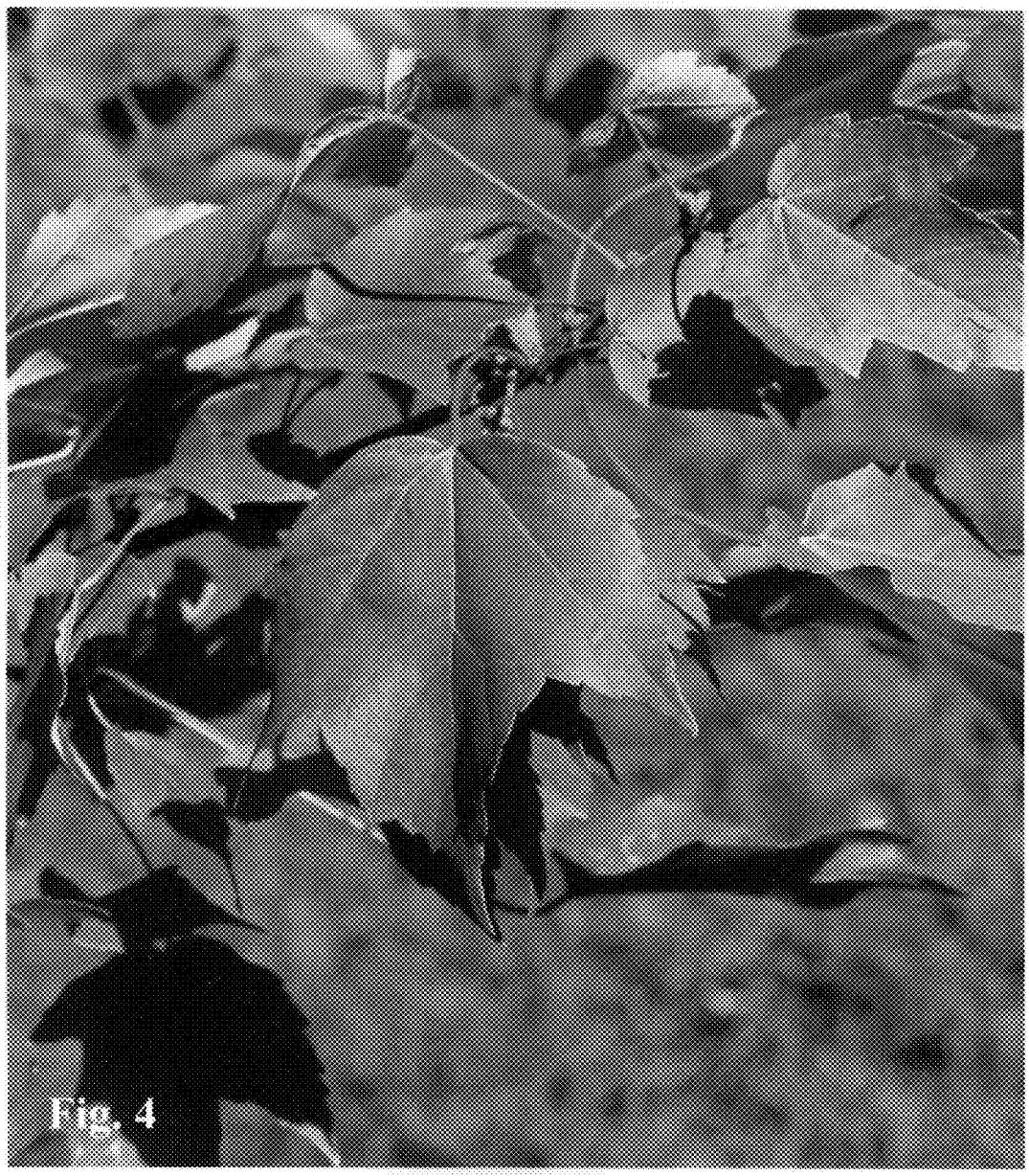
FIG. 4 depicts the summer foliage of the 'Miller' cultivar, showing the absence of powdery mildew which is typical of all the leaves.

In the following description, color references are made to The Royal Horticultural Society Colour Chart published in 1966.

THE PLANT

Tree, Red Maple 'Miller'

Name: Cultivar 'Miller'.

Parentage: Seedling or Sport: Seedling estimated 1969. Seed parent: *Acer rubrum* unknown parent. Pollen parent: *Acer rubrum* unknown parent.

Classification: Botanic name: *Acer rubrum.*

Discovered: In a cultivated area, at 846 Hoagland Road, Jacksonville, Ill. 62650. Tissue culture and rooting of softwood cuttings have been used to asexually propagate the 'Miller' cultivar. Presently, propagation is being performed at 846 Hoagland Rd, Jacksonville, Ill. 62650 and at several nurseries in Oregon.

Form: Tree.

Shape: Decurrent, Broadly spreading.

Height: 11 m (36').

Spread: 11 m (36').

Trunk size: 38 cm (15") diameter at 137 cm (4.5') above ground level.

Base: Cylindrical.

Growth rate: Fast, with good vigor.

Strength: Good.

Age: Approximately 44 years.

Bark (trunk): Grey-green (197A, B, & C) medium in texture, breaking into thin plates.

Branches:

*Angle of attachment.*—Most branch angles were 45°, with lower branches at the base of the crown approaching 60°.

*Spacing.*—Close, most branches between 15.24 cm (6 inches) to 30.48 cm (12 inches) spacing.

*Bark color.*—Grey (201B and 201C).

*Bark texture.*—Smooth with no exfoliation. Small Twig Bark: Texture: rough and warty, with lenticels.

*Twig bark color.*—(Growing season) grey-orange (174A) and grey-orange (175A) (dormant season) grey-white (156D).

*Lenticels.*—Small ranging from (0.05-0.16 cm) in length, average 0.12 cm, scattered, elliptical, raised, color grey-orange (175 B&C).

*Small branch bark.*—(≥2.54 cm diameter) moderately rough texture with a vertical pattern of ridges, mottled color with grey-green (201C&D) as well as (197C&D).

Leaves:

*Petiole.*—Length: (3.3-11.75 cm), average 7.6 cm in length. Color: Summer color: yellow-green (154D). Autumn color: grey-purple (185A). Texture: mostly smooth with some small warts.

*Lamina.*—Length: (6.19-10.8 cm), average length 8.4 cm. Width: (3.8-12.7 cm), average width 8.2 cm. Form: overall shape of lamina: palmate. Shape of base: truncate to slightly cordate. Shape of apex: acute. Margin: coarsely toothed. Texture: membranous. Upper surface: smooth. Lower surface: smooth. Quantity: abundant. Color: spring upper side: grey-purple (185A) after bud break transitioning to yellow-green (154A). Lower side: grey-purple (186D) transitioning to yellow-green (154C). Summer upper side: green (143A). Lower side: yellow-green (148D). Autumnal upper side: red (45C&D), grey-purple (185A). Lower side: grey-purple (186D&C). Ribs and veins: number of pairs: 3 main veins. Venation pattern: palmate. Vein color: yellow-green (154D).

Buds: (Vegetative) (0.37-0.53 cm) in length, average 0.48 cm long, grey-orange (146B, C, & D) in color, with 2-4 pairs of imbricate scales with some pubescence.

Flowers: Monoecious, polygamous with perfect and staminate flowers appearing just before the unfolding of the new leaves. Flowers are red in color (45A & B).

Fruit: Samara, average 2.5 cm in length.

Figure 5:
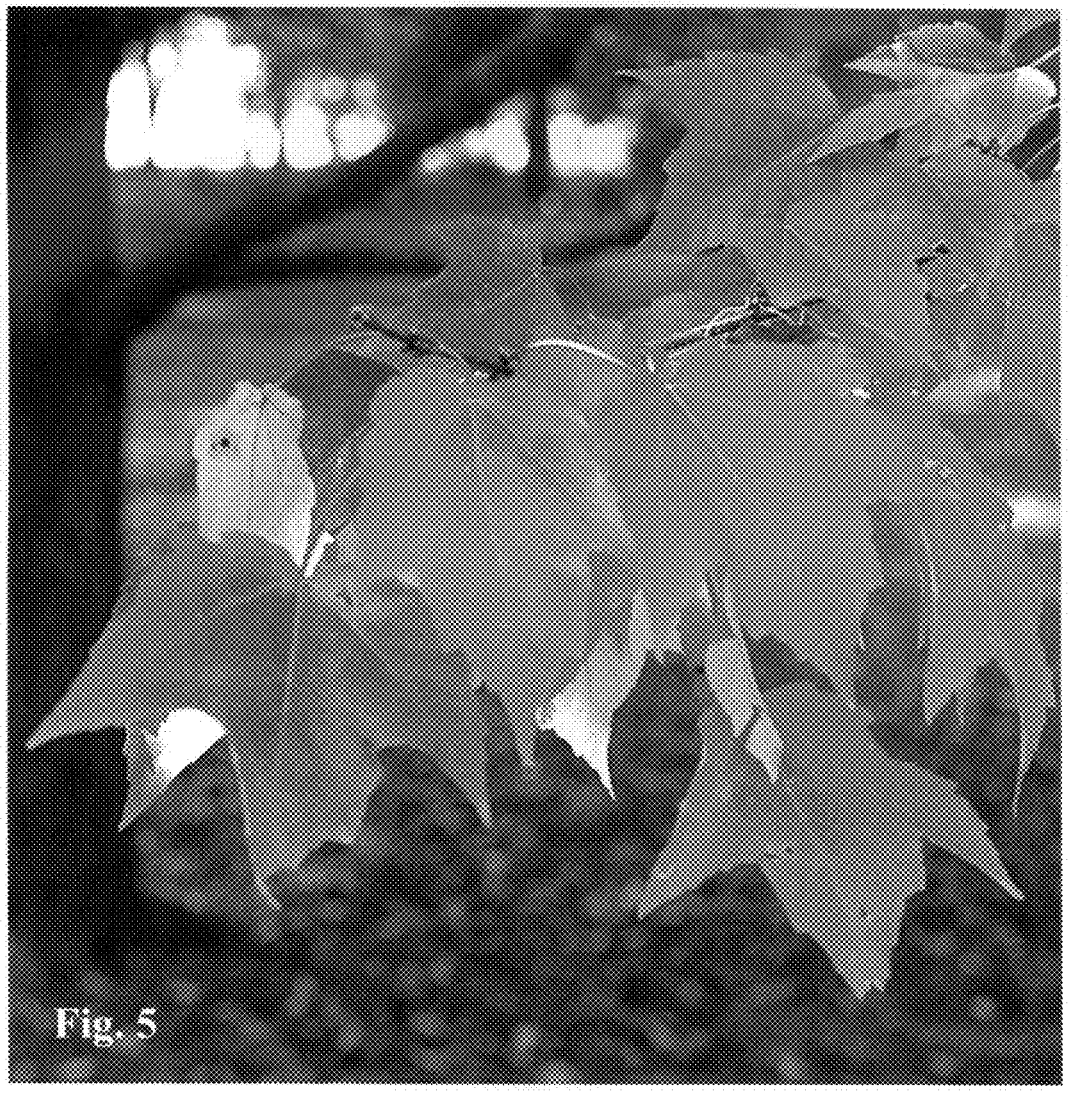
FIG. 5 depicts autumn foliage of the 'Miller' cultivar.
Figure 6:
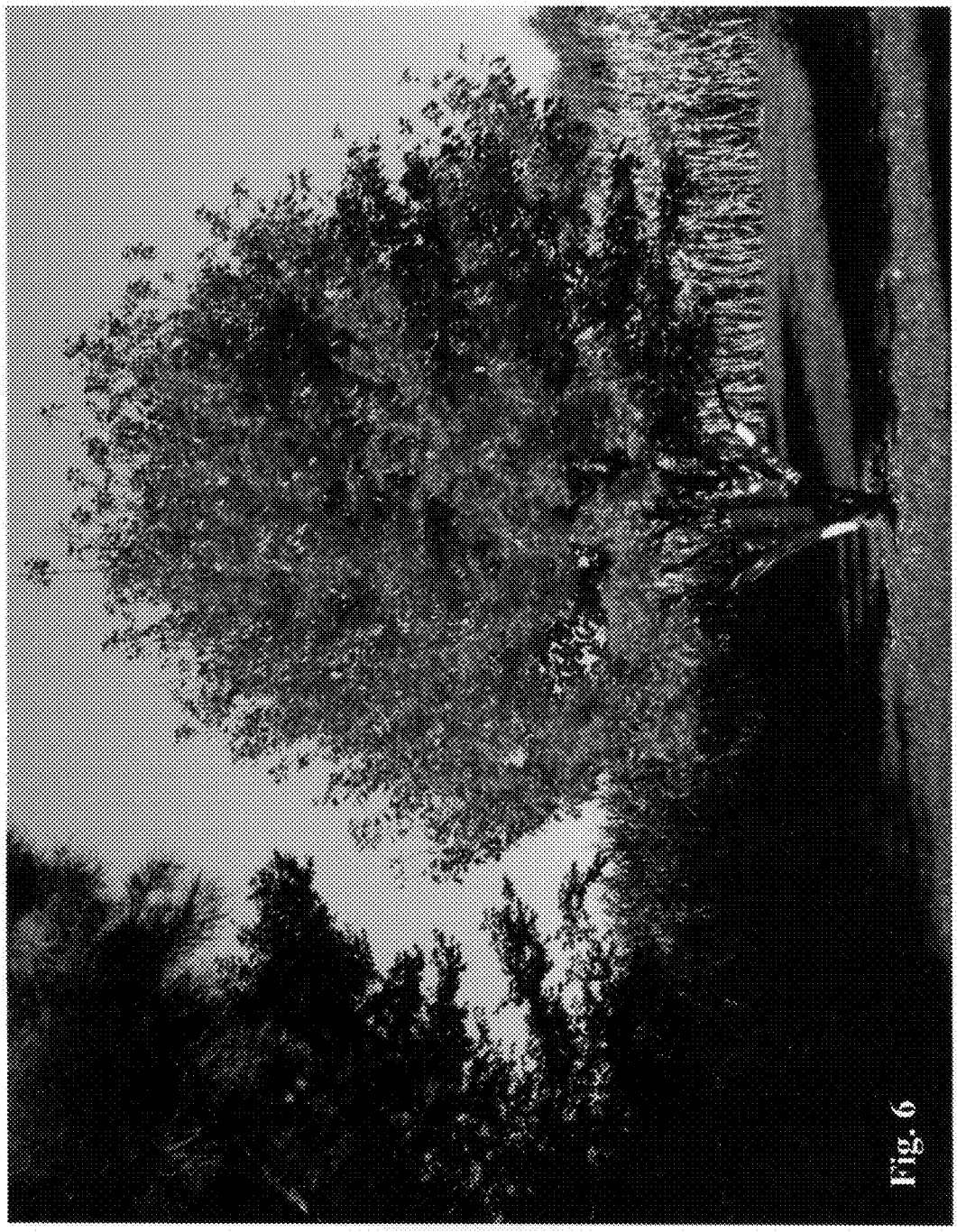
FIG. 6 depicts the first asexually propagated tree of the 'Miller' cultivar at 15 years old with autumn foliage that colors as intensely as the parent plant.

This cultivar displays a symmetrically rounded crown enhanced by clean, green summer foliage and pleasing early, scarlet red autumn foliage. It has excellent strength, with no visible signs of broken branches or pockets of rot in the crown, excellent hardiness, and drought tolerance. This red maple has good cold and drought tolerance which is typical of the species. The 'Miller' cultivar has experienced low temperatures of −28° F. without any damage. This cultivar differs from other red maple by exhibiting early fall color that begins in late September in central Illinois. In contrast, October Glory® and Red Sunset® 'Franksred' develop fall color in mid to late October. The 'Miller' red maple cultivar has scarlet red autumn foliage (FIG. 5) until leaf drop. This characteristic differs from 'Magnificent Magenta' autumn foliage that changes from burgundy to scarlet before leaf drop.

It is claimed:

1. A new and distinct cultivar of red maple tree *Acer rubrum*, named 'Miller' as illustrated and described.

* * * * *